(12) United States Patent
Choubey et al.

(10) Patent No.: US 9,408,777 B2
(45) Date of Patent: Aug. 9, 2016

(54) BLISTER PACKAGE FOR PATIENT COMPLIANCE

(75) Inventors: Pravir Choubey, Aurangabad (IN); Yogita Kodgule, Aurangabad (IN)

(73) Assignee: WOCKHARDT LIMITED, Bandra East, Mumbai (IN)

( * ) Notice: Subject to any disclaimer, the term of this patent is extended or adjusted under 35 U.S.C. 154(b) by 0 days.

(21) Appl. No.: 14/237,874

(22) PCT Filed: Aug. 6, 2012

(86) PCT No.: PCT/IB2012/054003
§ 371 (c)(1),
(2), (4) Date: Feb. 19, 2014

(87) PCT Pub. No.: WO2013/030697
PCT Pub. Date: Mar. 7, 2013

(65) Prior Publication Data
US 2014/0183095 A1    Jul. 3, 2014

(30) Foreign Application Priority Data
Aug. 26, 2011   (IN) .......................... 2394/MUM/2011

(51) Int. Cl.
*A61J 1/03* (2006.01)
*B65D 75/32* (2006.01)
*A61J 7/04* (2006.01)

(52) U.S. Cl.
CPC .. *A61J 1/035* (2013.01); *A61J 7/04* (2013.01); *B65D 75/327* (2013.01)

(58) Field of Classification Search
CPC ............... A47J 1/00; A47J 1/03; A47J 1/035; A47J 7/0084; A47J 7/04; A47J 7/0481; A47J 2007/0454; B65D 75/327; B65D 85/42; B65D 83/0445; B65D 83/0481; B65D 83/04
See application file for complete search history.

(56) References Cited

U.S. PATENT DOCUMENTS

| | | | |
|---|---|---|---|
| 4,473,156 A * | 9/1984 | Martin ........................... | 206/534 |
| 6,375,956 B1 | 4/2002 | Hermelin et al. | |
| 6,681,935 B1 * | 1/2004 | Lewis ............................ | 206/534 |
| 7,328,802 B2 | 2/2008 | Killinger | |
| 7,866,476 B2 * | 1/2011 | McGonagle ............ | A61J 1/035 206/472 |
| 2002/0045184 A1 * | 4/2002 | Chen ................................. | 435/6 |
| 2004/0171992 A1 | 9/2004 | Formby | |

(Continued)

FOREIGN PATENT DOCUMENTS

| | | |
|---|---|---|
| BE | 29913195 U1 | 2/2000 |
| FR | 2705886 A1 | 12/1994 |

*Primary Examiner* — Anthony Stashick
*Assistant Examiner* — Mollie Llewellyn
(74) *Attorney, Agent, or Firm* — Bio Intellectual Property Services LLC (Bio IPS); O. (Sam) Zaghmout (57) ABSTRACT

This invention relates to a compliance blister package comprising a matrix of blisters arranged in a plurality of columns and plurality of rows which comprises a combination of one of the fixed dose combination dosage form comprising two or more therapeutically active ingredients loaded into blisters of one of the columns and the other dosage form which comprises one or more of therapeutically active ingredient form loaded into the successive column blisters for once a day administration or concurrent administration.

5 Claims, 7 Drawing Sheets

(56) References Cited

U.S. PATENT DOCUMENTS

| | | | |
|---|---|---|---|
| 2005/0087474 A1* | 4/2005 | Killinger | 206/538 |
| 2006/0144749 A1* | 7/2006 | Arnold et al. | 206/538 |
| 2007/0015839 A1* | 1/2007 | Folli et al. | 514/635 |
| 2007/0184078 A1 | 8/2007 | Chen | |
| 2009/0139893 A1 | 6/2009 | McGonagle | |
| 2009/0272081 A1* | 11/2009 | Panson et al. | 53/467 |

* cited by examiner

BLISTER PACKAGE FOR PATIENT COMPLIANCE

FIELD OF THE INVENTION

This invention relates to a compliance blister package comprising a matrix of blisters arranged in a plurality of columns and plurality of rows which comprises a combination of one of the fixed dose combination dosage form comprising two or more therapeutically active ingredients loaded into blisters of one of the columns and the other dosage form which comprises one or more of therapeutically active ingredient form loaded into the successive column blisters for once a day administration or concurrent administration; and the compliance blister package is identifiable by the product name, the product strength, the lot number, the expiry date and order time for patient compliance.

BACKGROUND OF THE INVENTION

Non-compliance is generally associated with patients having chronic illness or illnesses such as hypertension, diabetes, psychotics, hypercholesterolemia etc. The reasons for non compliance are many which include multiple medication administration, complex treatment regimens, frequent dose regimens, increasing numbers of medication prescribed and the increase in side effects and/or drug interactions associated with multiple drug regimens.

Studies have reported that non compliance increases when the number of tablets or capsules taken daily increases from one to four times daily (Galley, M. S. To be taken as directed. JIR Coll Gen Pract, 1968, 16, 39-44. Eisen, S. A. et al., Arch Intern Med 150, p. 1881, 1990. "The administration of medication at frequent intervals makes it more likely that the patient's normal routine or work schedule will have to be interrupted to take a dose of medication and in many cases the patient will forget, not want to be inconvenienced or be embarrassed to do so." Remington's Pharmaceutical Sciences, Chpt. 103, Vol. II, p. 1800 (19th Ed. 1995).

The Physician's and pharmacist's relationship with the patient will influence medication compliance. For example, how clearly the physician and/or pharmacist explain the treatment regimen to the patient being treated will influence how likely the patient will comply with the drug therapy prescribed.

Medication compliance aids have been developed to enhance compliance. In medicine, compliance (also adherence, concordance, or capacitance) describes the degree to which a patient correctly follows medical advice. Most commonly, it refers to medication or drug compliance, but may also mean use of medical appliances such as compression stockings, chronic wound care, self-directed physiotherapy exercises, or attending counseling or other courses of therapy. One example is a compliance package. A compliance package may be defined as "a prepackaged unit that provides one treatment cycle of the medication to the patient in a ready-to-use package"

U.S. Pat. No. 7,328,802 provides a child resistant blister packages utilizing walled structures enclosing medicament therein.

US Application No. 20080190801 relates to pharmaceutical packaging systems or improved patience compliance.

US Application No. 20070093497 relates to methotrexate compliance package.

WO98/22072 relates to compliance package and method of improving or aiding patient compliance for complex drug regimens.

Some of the prior art compliance packages are; For example, OvconX 35 and 50 (Bristol-Meyers Squibb), Ortho-Novum Dialpak 1/35, 1/50, 10/11 and 7/7/7 (Ortho Pharmaceutical Corp.), Loestrin (D Fe 1/20 and 1.5/30 (Parke-Davis), etc. are oral contraceptives packaged in blister cards. These packages are generally a single blister card, with 21 or 28 day regimens; RheumatrexQ) Dose Packs made by Lederle Laboratories, containing four blister-pack cards each containing either 2, 3, 4, 5, or 6 tablets (for 5 mg, 7.5 mg, 10 mg, 12.5 mg, or 15 mg per week, respectively) for 1-week's therapy of methotrexate; Medrol Dosepak (Upjohn Company), is a packaging designed for the administration of steroids, (i.e. methylprednisolone) which require staggered dosing. For each day of drug treatment the number of tablets (and total dose) that the patient must take, decreases. For example, the Medrol Dosepak contains 21, 4 mg tablets for 6 days of treatment where for each day of treatment, the total daily dose decreases by one tablet; ZithromaxX Z-Pak made by Pfizer Laboratories, contains a single medication blister card with 6, 250 mg capsules. Each blister medication card is labeled with "Day 1 to Day 5" for each dose, the first dose being two, 250 mg capsules labeled "Day 1." Each subsequent capsule is labeled with "Day 2" to "Day 5."

SUMMARY OF THE INVENTION

The present inventors have found a need for a suitable compliance blister package which caters not only to once a day administration of fixed dose combination of a therapeutically active ingredient but also concurrent administration of a combination of therapeutically active ingredients.

The present inventors while working on a compliance blister package have surprisingly designed a simple, cost effective, and simple to use blister pack design. The blister pack design of the present invention aids in increasing patient compliance for multiple medication administration, complex treatment regimens, and frequent dose regimens by reduced frequent dose regimens, easy to use by elderly patient's declining mental functioning, increasing numbers of medication prescribed for any single day and the need for incorporating reduced side effect multiple combinations of therapeutically active ingredients.

In one of the aspects of the invention a compliance blister package for patient compliance is provided with the dosage of medication over a period of time; the package comprises a base having a matrix of blisters; said matrix including a plurality of columns and a plurality of rows; A plurality of set of dosage forms are provided in the blisters; each dosage form is loaded into blister of one of an adjacent row and an adjacent column; Each column blister is identifiable by a unique color provided over the tear away or peel away backing strip; Each column tear away or peel away backing strip color may be one or more of white, grey, yellow, blue, green, orange, violet and indigo. Each row blister has days of the week printed on its backing strip; the backing strip color of the successive columns may be different for easy identification by the patient; the compliance blister package is characterized in that the same set of dosage forms are loaded into the successive columns blisters for administration or a combination of more than one dosage form in successive columns blisters of which one of the dosage forms comprises the fixed dose combination in one of the columns blister and the other dosage form comprising one or more of therapeutically active ingredients in the successive column blister for concurrent administration; each dosage form in a set comprises a common dose of medication comprising fixed dose combination of two or more therapeutically active ingredients for administration and a combination of fixed dose combination in one set and one or more therapeutically active ingredient in another set; the columns represent the week and the rows days of the week; each successive column blister represent successive week from left to right; Each successive row blister represent successive days of the week starting from top to bottom; successive column blister is identifiable by a unique color provided over the tear away or peel away backing strip; Each successive column tear away or peel away backing strip color may be one or more of white, grey, yellow, blue, green, orange, violet and indigo; the backing strip color of the successive columns may be different for easy identification by the patient in compliance blister pack of administration or concurrent administration; each row blister represent successive days of the week; the blister comprises dosage forms for once a day administration of the medication; and the blister package is identifiable by the product name, the product strength, the lot number, the expiry date and the order time in the last row.

One of the eighth row blisters of the compliance package may be used to load the last dose and the other to represent the approach time for the next order.

Figure 7:
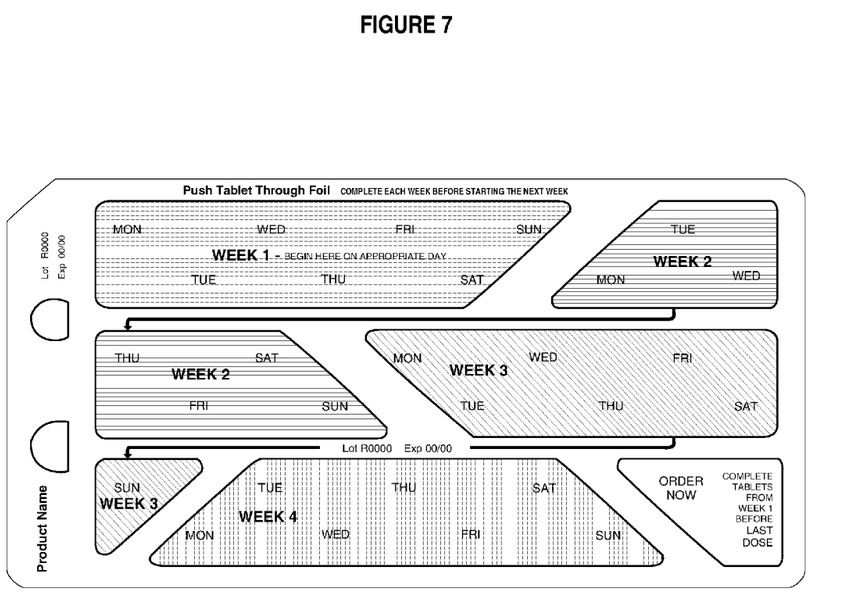
FIG. 7 Illustrates an embodiment of blister package comprising a fixed dose combination of two or more therapeutically active ingredients for administration herein the blisters arranged in a staggered manner.

In another aspect of the invention a compliance blister package for patient compliance is provided with the dosage of medication over a period of time; the package comprises a base having a matrix of blisters; said matrix including a plurality of columns and a plurality of rows; A plurality of set of dosage forms are provided in the blisters; each dosage form is loaded into blister of one of an adjacent row and an adjacent column; the plurality of columns blisters and rows blisters are arranged in a staggered manner; a geometrical shape (as shown in FIG. 7) formed as a consequence of arrangement of a week's once a day administration of dosage forms in blisters may further be facilitated easy recognition by the use of a specific color for tear away or peel away backing sheet corresponding to the geometrical shape. The color on the tear away or peel away backing strip color may be one or more of white, grey, yellow, blue, green, orange, violet and indigo. Each blister comprising the dosage form comprising two or more therapeutically active ingredient in a staggered manner may easily be identified by the day of the week. The week of the month may easily be identifiable by the prominent display centrally in the space available between the staggered blisters. The staggered arrangement of a week's once a day administration of dosage forms in blisters necessitates formation of different geometric shape of the blisters on the tear away or peel away backing sheet; As a consequence of limitation imposed on the size in longitudinal and horizontal direction for easy handling of the compliance blister package, which is intended to accommodate a month's dosage form, a week's dosage form for administration may have to be fragmented into two different geometric shapes of which one of the geometric shapes comprises at least one and at most four blisters and the other geometric shape comprises the balance number of blister required for the week i.e. from three to six blisters; The administration of a month's dosage forms by the arrangement of blisters in a staggered manner results in two different easily identifiable geometric shapes formed on the tear away or peel away backing sheet per horizontal row. The details of the geometrical shape and the arrangement of blisters are shown in FIG. 7.

The details of one or more embodiments of the inventions are set forth in the description below. Other features, objects and advantages of the invention will be apparent from the description and claims.

DETAILED DESCRIPTION OF THE DRAWINGS

FIG. 6 Illustrate an embodiment of blister package comprising a fixed dose combination of two therapeutically active ingredients for administration incorporating tear able feature to the blister;

DETAILED DESCRIPTION OF THE INVENTION

The following terminologies will have the meanings as defined below.

The term "active ingredient" refers to a therapeutically active compound, as well as any prodrugs thereof and pharmaceutically acceptable salts, hydrates and solvates of the compound and the prodrugs.

The term "blister" as used herein refers to a reservoir or pocket or cell of the compliance package which accommodates the active ingredient in any of the dosage form as defined under "dosage form".

The term "fixed dose combination" product as used herein refers to a combination of two or more separate drug ingredients, combined in a single dosage form, in defined doses.

The "dosage form" as defined here is in the form of a tablet or capsule of any geometrical shape.

"Administration" as used herein refers to once a day administration of a single drug.

"Concurrent administration" as used herein refers to once a day administration of more than one single drug overlapping on the same day.

The "Successive column" blister as used herein refers to the blister comprising the dosage form comprising the same active ingredient in each of the successive columns as it was in the previous regime. For example if there are two dosage forms and each of the dosage forms comprise different active ingredients for concurrent administration, then the third and fourth columns represent the successive columns for the dosage forms loaded in the first and second column initially. If there is only one dosage form for administration in the compliance package, then each of the columns represent successive column for the previous one.

Figure 1:
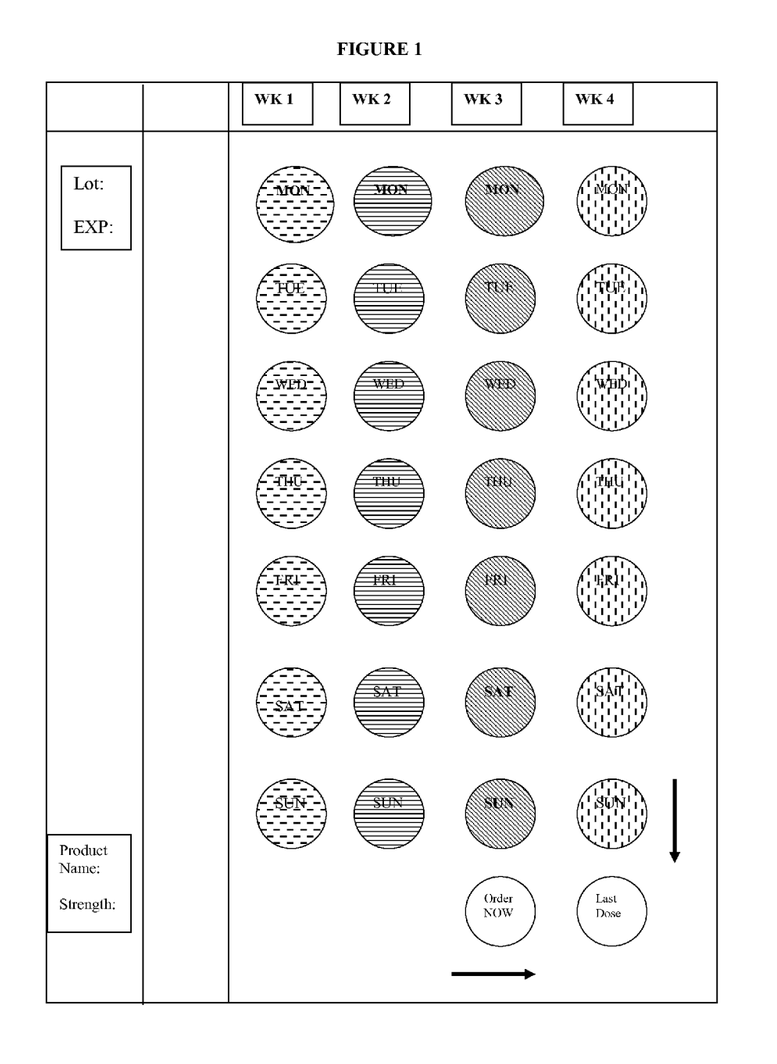
FIG. 1 Illustrate an embodiment of blister package comprising a fixed dose combination of two therapeutically active ingredients for administration.
Figure 2:
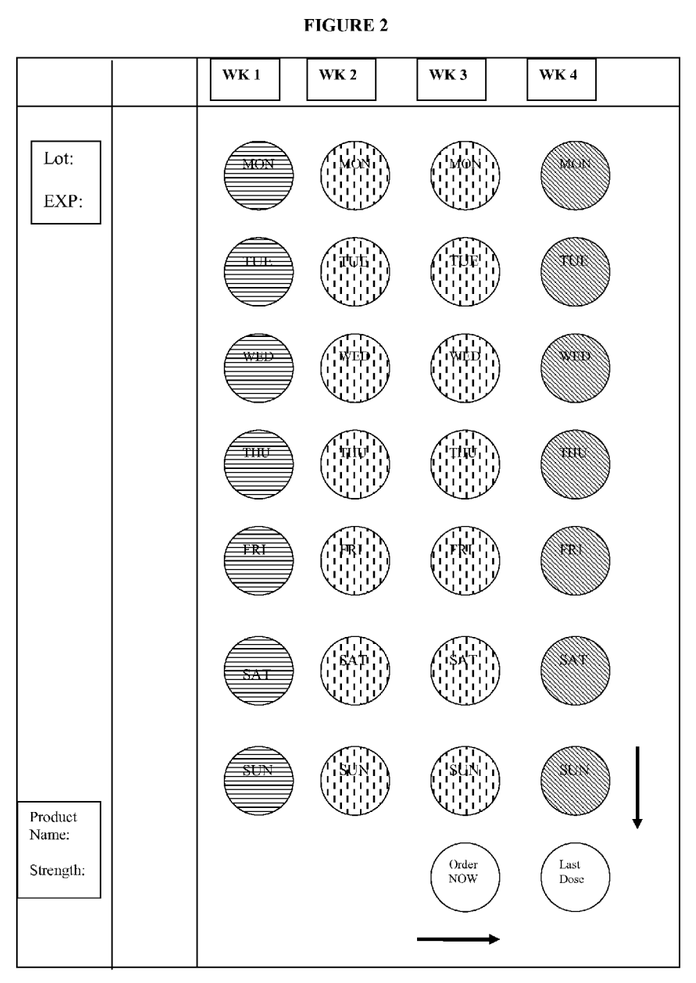
FIG. 2 Illustrate an embodiment of blister package comprising a fixed dose combination of three therapeutically active ingredients for administration.

In one of the aspects of the invention is provided a compliance blister package for patient compliance with the dosage of medication for administration over a period of time. The compliance blister package may comprise a base having a matrix of blisters; said matrix may include a plurality of columns and a plurality of rows. Columns may represent week and rows days of the week. The number of column blisters in a compliance package may be one or more and may be of even number or odd number. The rows of blisters in compliance package maybe seven or more. Seven row blisters represent seven days of the week. Eighth row blisters represent the approach order time or loading the last dose dosage form. Alternatively blister rows may represent the week and blister columns days of the week. One of the embodiments of the compliance package of this design is enumerated in FIG. 5. A plurality of set of dosage forms may be provided in the blisters. Each dosage form may be loaded in blister of one of an adjacent row and an adjacent column Each dosage form in a set of a compliance blister package may comprise a common dose of medication which comprises two or more therapeutically active ingredients. The columns blister represents the week and the rows days of the week. Each successive column blister starting from left to right of the compliance package may represent successive week. Each successive row blister from top to bottom of the compliance package may represent successive days of the week. The blisters may comprise dosage forms for once a day administration of the medication. FIG. 1 illustrates an embodiment of a blister package which comprises a fixed dose combination of two therapeutically active ingredients for administration. FIG. 2 illustrate an embodiment of blister package which comprises a fixed dose combination of three therapeutically active ingredients for administration. Abbreviated week days have been shown against each row. WK 1, Wk 2 etc refer week 1, week 2 etc and so on in FIGS. 1 to 4.

In one of the embodiments each dosage form in a set of a compliance blister package shown in FIG. 2 may comprise a common dose of medication which comprises a combination of a fixed dose combination of metoprolol and salts and one or more of ace inhibitors, angiotensin II receptor blocker, and calcium channel blocker i.e. may refer to any one or more of ace inhibitors, angiotensin II receptor blocker, and calcium channel blocker.

Figure 3:
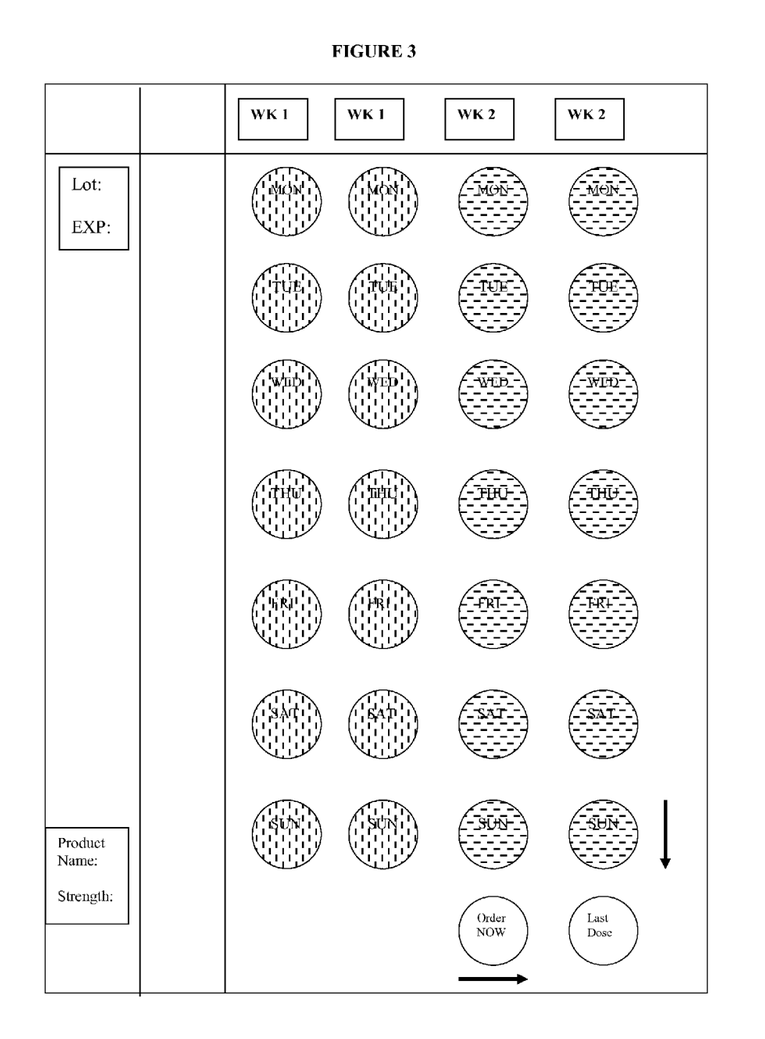
FIG. 3 Illustrate an embodiment of blister package comprising a combination of fixed dose combination of three therapeutically active ingredients and a therapeutically active ingredient for concurrent administration.
Figure 4:
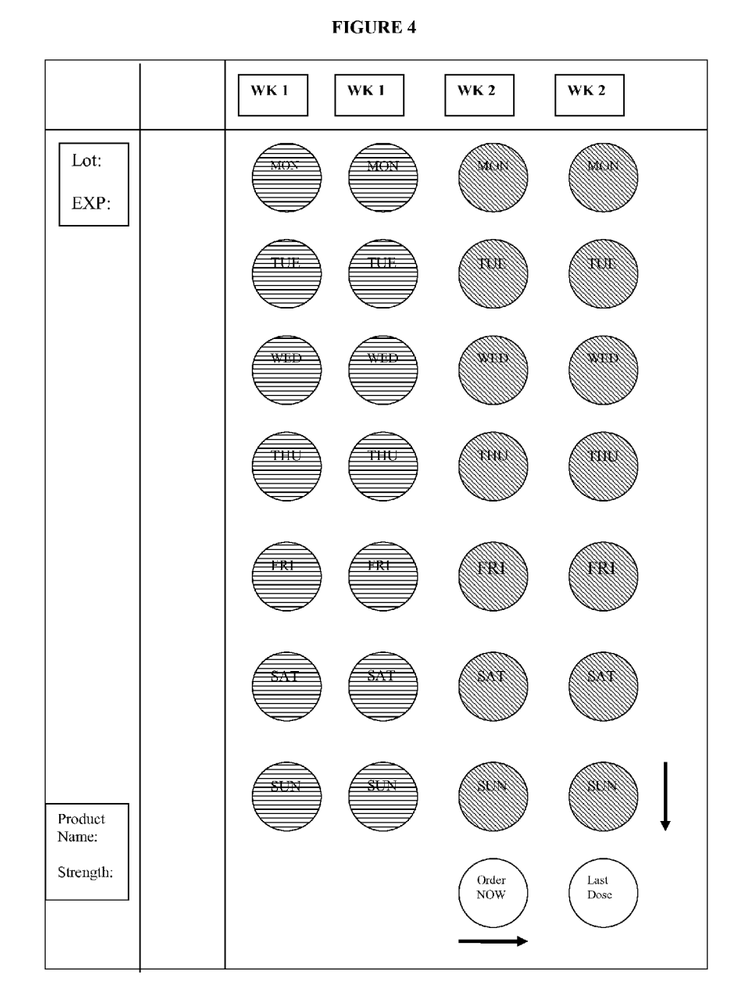
FIG. 4 Illustrate an embodiment of blister package comprising two different fixed dose combinations of two therapeutically active ingredients and for concurrent administration.

In another aspect of the invention is provided a compliance blister package for patient compliance with the dosage of medication for administration over a period of time. The compliance blister package may comprise a base having a matrix of blisters; said matrix may include a plurality of columns and a plurality of rows. Columns blister may represent week and rows blisters days of the week. Alternatively rows may represent week and columns days of the week. A plurality of set of dosage forms may be provided in the blisters. Each dosage form may be loaded in blister of one of an adjacent row and an adjacent column. Each dosage form in a set of a compliance blister package may comprise a common dose of medication for concurrent administration which comprises a combination of either two different fixed dose combination dosage forms separately or a fixed dose combination and one or more of therapeutically active ingredients in the other, of which one of the fixed dose combination dosage form may comprise at least two or more therapeutically active ingredients and the other dosage form may comprise at least one or more of therapeutically active ingredients. The columns blisters may represent week and the rows blisters days of the week. One of the fixed doses combination dosage form may be loaded in to the first column blister represented as WK 1 in FIG. 3. The other dosage form comprising either the fixed dose combination or one or more of the therapeutically active ingredients may be loaded into the second column blister represented as Wk 2 in FIG. 3 & FIG. 4. The successive column blister which comprises one of the fixed dose combinations of the same dosage form may represent successive week for that fixed dose combination. Similarly, the successive column blister which comprises the other dosage form which comprises one or more of therapeutically active ingredients or the other fixed dosage form may represent the successive week for the other dosage form or the fixed dose combination dosage form as the case may be. The starting column blisters and the next to it column blisters represent week 1 in respect of concurrent administration of two different dosage forms. The subsequent two columns i.e. the third and fourth blisters represent week 2 as shown in FIG. 3 and FIG. 4 in respect of concurrent administration of two different dosage forms.

Figure 5:
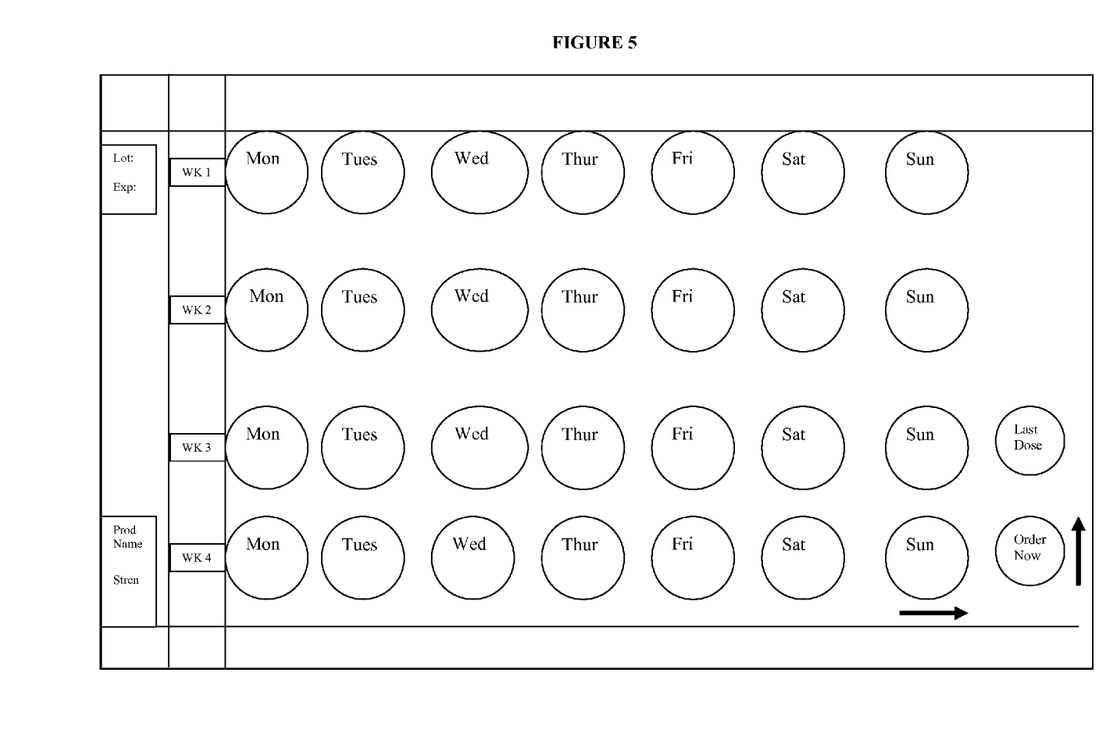
FIG. 5 Illustrate an embodiment of blister package comprising a fixed dose combination of two therapeutically active ingredients for administration.

FIG. 5 Illustrate an embodiment of blister package comprising a fixed dose combination of two therapeutically active ingredients for administration; FIG. 6 Illustrate an embodiment of blister package comprising a fixed dose combination of two therapeutically active ingredients for administration incorporating tear able feature to the blister;

FIG. 7 illustrates an embodiment of blister package comprising a fixed dose combination of two or more of therapeutically active ingredients for once a day administration loaded into the blisters arranged in a staggered manner. It may be observed a compliance package comprising once a day administration of fixed dose combination comprising two or more therapeutically active ingredients loaded into blisters arranged in staggered manner; this arrangement of blisters in a staggered manner may result in horizontal rows of specific geometric shapes formed on the backing sheet; each row comprising at least two specific geometric shapes; further at most two different geometric shapes may represent a week's administration of dosage forms; there may be three distinguishable horizontal rows comprising different geometric shapes comprising blisters;

The compliance package of the invention is also intended to include concurrent administration of more than two different dosage forms. For example a compliance package comprising three different dosage forms wherein one of the dosage forms comprises fixed dose combination comprising two or more than two therapeutically active ingredients and two other dosage forms comprise a combination of fixed dose combination and one or more therapeutically active ingredients may be loaded into each of the first second and third columns blisters for concurrent adminstration during the first week. Fourth, fifth and sixth successive columns blister may be loaded with the above dosage forms for concurrent administration during the second week and so on.

The blister package may be any known child resistant or non child resistant one. The blister package is provided in a carton cover or carton box.

In one of the aspects of the invention one or more of therapeutically active ingredients and combination thereof in the compliance blister package may be antihypertensive, platelet aggregation inhibitors, antidiabetics and anti psychotic, anti-inflammatory agents, sedatives, hypnotics, antibiotics, anti-osteoporosis agents, antithrombotic agents, antivirals, antifungals, anticholinergic agents, anxiolytic agents, adrenergics, anti-parkinsonism agents, anticonvulsants, antiepileptics, CNS stimulants, antianginal agents, antiarrhythmics, antihyperlipidemic drugs, diuretics, antiasthmatics, anticoagulants, antianemia agents, vitamins, hormones, antihistaminics, anticancer agents, antiallergics, antiarthritis agents, antialzheimers' agents, vasopressin antagonists, anticonvulsants, steroids, anesthetics, thrombolytics, antacids, proton pump inhibitors, protease inhibitors, mucolytics, antimalarials, antiemetics, laxatives, expectorants, enzymes, contraceptives, bronchodilators, antitussives, antimigraine agents, anthelmintics, antidepressants, and anorexiants within the scope of the invention.

While the present invention has been described in terms of its specific embodiments, certain modifications and equivalents will be apparent to those skilled in the art and are intended to be included within the scope of the invention.

We claim:

1. A blister package for patient compliance with a dosage form; the blister package comprising a matrix of blisters; said matrix including a plurality of columns and a plurality of rows; each blister comprising a single dosage form for once a day administration; said column blisters representing a week and the row blisters representing days of the week; two adjacent columns form a group, with each group representing a week and each column of the group comprising a different dosage form; the dosage form in one column of the group comprising a fixed dose of metoprolol or salts thereof and the dosage form in the adjacent column of the group comprising a platelet inhibitor; each blister is printed with the day of the week on a backing strip; the backing strip is identifiable by a unique color selected from white, grey, green, orange, violet and indigo; the blister package is printed with a product name, a product strength, a lot number, an expiry date, an order time and last dose indication.

2. The blister package of claim 1, wherein the dosage form in one column of the group further comprises one or more therapeutically active ingredients selected from ace inhibitors, angiotensin II receptor blockers and calcium channel blockers, in addition to the metoprolol or salts thereof.

3. The blister package of claim 1, wherein the backing strip is a tear away or a peel away strip.

4. The blister package of claim 1, wherein the blister package is child resistant.

5. The blister package of claim 1, wherein the blister package is non child resistant.

* * * * *